United States Patent [19]
Levin

[11] Patent Number: 5,295,990
[45] Date of Patent: Mar. 22, 1994

[54] TISSUE SAMPLING AND REMOVAL DEVICE

[76] Inventor: John M. Levin, 412 Fairview Rd., Penn Valley, Pa. 19072

[21] Appl. No.: 943,660

[22] Filed: Sep. 11, 1992

[51] Int. Cl.⁵ ............................................. A61B 10/00
[52] U.S. Cl. ........................................ 606/49; 128/751
[58] Field of Search ............... 128/749, 751, 783, 784, 128/786; 606/51, 49, 52, 170, 205–208

[56] References Cited

U.S. PATENT DOCUMENTS

| | | | |
|---|---|---|---|
| 3,895,636 | 7/1975 | Schmidt | 128/305 |
| 3,934,115 | 1/1976 | Peterson | 219/223 |
| 4,522,206 | 6/1985 | Whipple et al. | 128/312 |
| 4,655,216 | 4/1987 | Tischer | 606/51 |
| 4,785,825 | 11/1988 | Romaniuk et al. | 128/751 |
| 4,815,476 | 3/1989 | Clossick | 128/751 |
| 4,817,630 | 4/1989 | Schintgen et al. | 128/751 |
| 4,881,550 | 11/1989 | Kothe | 128/752 |
| 4,887,612 | 12/1989 | Esser et al. | 128/751 |
| 4,953,559 | 9/1990 | Salerno | 128/751 |
| 5,052,402 | 10/1991 | Bencini et al. | 128/751 |
| 5,074,311 | 12/1991 | Hasson | 606/170 |
| 5,085,659 | 2/1992 | Rydell | 606/170 |
| 5,147,357 | 9/1992 | Rose et al. | 606/49 |

FOREIGN PATENT DOCUMENTS 2355521 1/1978 France ................................. 606/52

Primary Examiner—Max Hindenburg
Attorney, Agent, or Firm—Caesar, Pivise, Bernstein, Cohen & Pokotilow, Ltd.

[57] ABSTRACT

A device for removing a tissue portion and cauterizing surrounding tissue, includes a pair of cutting jaws having a heat-insulated inner surface defining a chamber for retaining tissue cut by the jaws. The device includes actuating means for pivoting the cutting jaws between opened and closed positions, and a control means for directing cauterizing current to the jaws when the jaws in a closed position, to thereby cauterize tissue surrounding the jaws.

4 Claims, 1 Drawing Sheet

TISSUE SAMPLING AND REMOVAL DEVICE

BACKGROUND OF THE INVENTION

This invention relates to tissue sampling and removal devices, and more particularly, to biopsy and/or resecting devices which are used to obtain a tissue sample or portion, and cauterize surrounding tissue while the tissue portion is protected from the cauterization process.

Various types of tissue sampling and removal devices are shown in the prior art. For example, the following United States patents, the entire disclosures of which are incorporated herein by reference, disclose forceps having jaws in the form of a spoon or cup-shaped element with a cutting edge about the periphery for both severing a tissue specimen and retaining the specimen within the jaws after they are closed: 3,895,636 (Schmidt); 4,522,206 (Whipple et al.); 4,785,825 (Romaniuk et al.); 4,815,476 (Clossick); 4,817,630 (Schintgen et al.); 4,881,550 (Kothe); 4,887,612 (Esser et al.); 4,953,559 (Salerno); and 5,052,402 (Bencini et al.).

Devices of the type disclosed in the foregoing patents exemplify sample or exploratory excision forceps, which are introduced into the human body, pinch or cut off a tissue sample and hold the sample on removing the forceps. The tissue sample is then placed on a corresponding substrate, for further analysis.

After the tissue sample is excised, bleeding usually occurs at the excision site. Various methods and devices can be used to cause the bleeding to stop, such as application of pressure, suturing or cauterization. A number of the foregoing methods and means for causing the bleeding to cease requires post-excision procedures, which requires the insertion of other instruments into the body at the excision site.

Utilizing the device of this invention, excision of tissue, retaining of the tissue and cauterization of the excision cite can be carried out with a single instrument, with cauterization taking place immediately after excision and without damage to the excised tissue. This expedites the entire procedure and ensures that cauterization will take place exactly at the excision cite. There is no damage to the excised tissue, since it is protected within an insulated chamber formed in the jaws of the biopsy device. The cauterization is accomplished by passing an electric current through the biopsy jaws, after excision has taken place.

U.S. Pat. No. 4,953,559 discloses electrically conductive cup-shaped members, which in their open position, function as a dipole for detecting electrical heart signals. These cup-shaped members also are insulated from each other through an insulating body and pin. However, this device does not disclose the use of an interior insulating surface of the cup-shaped members to protect a specimen from cauterizing current. Moreover, although the devices disclosed in Schmidt, Whipple et al. and Kothe utilize an arrangement of overlapping cutting edges, they as well do not utilize an interior insulated specimen retaining cavity.

U.S. Pat. No. 3,934,115 (Peterson) discloses an apparatus for electrical singe cutting of a thin material such as hair or paper. The Peterson device includes a tubular portion comprised of an insulating ceramic material which has a slot having stationary lined edges which are heated by electrical current to singe material within the slot. The Peterson device is not a tissue sampling device, and does not disclose a pair of jaws having insulated interiors.

Accordingly, a need exists for a device to obtain a tissue specimen to be used in variety of applications, while permitting the tissue surrounding the specimen to be cauterized without subjecting the specimen to the cauterization process.

OBJECTS OF THE INVENTION

Accordingly, it is a general object of this invention to provide a device for obtaining a tissue portion which overcomes the disadvantages of the prior art.

It is another object of this invention to provide a tissue sampling and removal device which permits the sampled tissue portion to maintain its integrity.

It is a further object of this invention to provide a tissue sampling and removal device which insulates the sampled tissue portion from the effects of cauterizing the surrounding tissue, when the sampled tissue portion is enclosed within the device.

SUMMARY OF THE INVENTION

These and other objects of this invention are achieved by providing a device to remove a tissue portion and cauterize surrounding tissue, while the tissue portion is housed within the device and protected from any effects of cauterization of the surrounding tissue. The device comprises a pair of jaws located at a first end of the device. The jaws are pivotally connected to permit the jaws to open and close. Each of the jaws has a recess formed therein, with the recess of each of the jaws mating to form an internal chamber when the jaws are closed. Each recess is lined with an insulating material, with the peripheral edges of the recesses being beveled to function as cutting edges. When the jaws are brought toward each other, the beveled edges remove the tissue sample, and retain it within the chamber formed by the mating insulating sections. An electrical current is then passed through the jaws, which cauterizes the tissue surrounding the removed tissue sample. The removed sample is maintained within the chamber formed by the two insulating lining sections.

DESCRIPTION OF THE DRAWING

Other objects and many attendant features of this invention will become readily appreciated as the same becomes better understood by reference to the following detailed description when considered in connection with the accompanying drawing, wherein.

DETAILED DESCRIPTION OF THE PREFERRED EMBODIMENT

Figure 1:
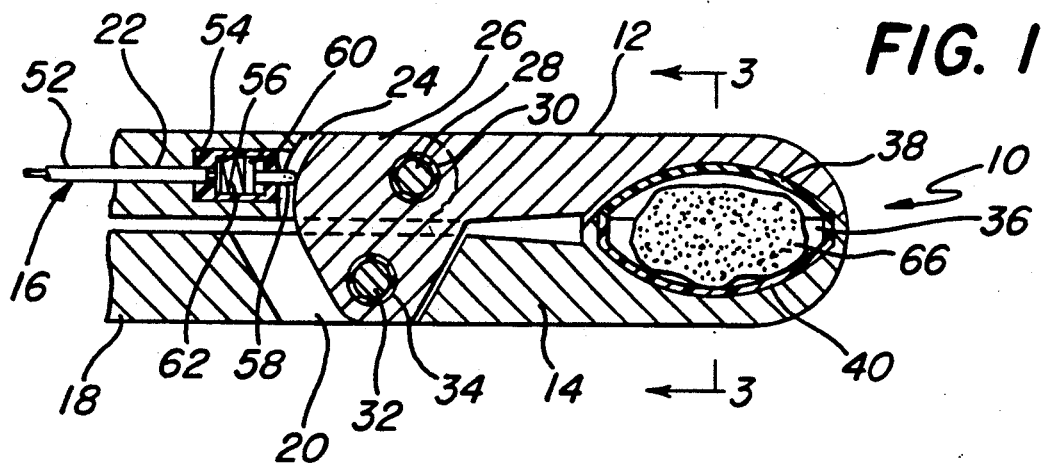
FIG. 1 is a side sectional view of a device constructed in accordance with this invention, in a closed position.

Referring now to various figures of the drawing where like reference numerals refer to like parts, a device constructed in accordance with this invention is generally shown at 10 in FIG. 1. Device 10 comprises a biopsy forceps usable in laparoscopic surgery, and having an upper jaw 12 and a lower jaw 14. A current supply assembly 16 is in contact with upper jaw 12.

Jaw 14 is formed at the end of rod 18. A recess 20 is formed in rod 18. Rod 22 is positioned on top of rod 18, and is longitudinally slidable relative thereto. A vertically extending slot 24 is formed in the forward end of rod 22. A rear tab 26 of upper jaw 12 is received in slot 24 and recess 20.

Upper jaw 12 is pivotally secured to rod 22 by pin 28. An insulating plastic sleeve 30 separates jaw 12 from pin 28. The lower end of tab 26 is pivotally secured to rod 18, within recess 20, by pin 32. An insulating plastic sleeve 34 separates pin 32 from tab 26.

A recess is formed in the forward end of each of the jaws 12 and 14. When the device 10 is in the position shown in FIG. 1, wherein the jaws are mating, the recesses form a chamber or cavity 36. The recess in jaw 12 is provided by a molded liner or coating 38 and the recess in jaw 14 is provided by a molded liner or coating 40. The recesses in jaws 12 and 14 terminate in beveled peripheral cutting edges 42 and 44, respectively. As seen in the enlarged section of the area 46 of FIG. 3, edges 42 and 44 mate when the jaws 12 and 14 are in the closed position shown in FIGS. 1 and 3, to thereby cut tissue to be retained within the cavity 36.

The liners or coatings 38 and 40 can be formed from any non-electrically conductive, insulating material, such as a ceramic, plastic or rubber material. A preferable material is a rigid plastic that can be formed into the cutting edges 42 and 44. Suitable plastics are polystyrene or polytetrafluoroethylene (Teflon). However, there are numerous other plastics that can be used for the same purpose. The liners can be secured to the inner walls of their respective jaws 12 and 14 by any means known to the art, such as by utilizing appropriate adhesives or by molding and heating in place.

The current supply assembly 16 includes electrical lead 52, which passes through a bore in rod 22. An insulating chamber 56 is placed within an enlarged bore in rod 22, which is in communication with slot 24. Lead 52 is electrically connected to plate 56, positioned within chamber 54. A pin 58 is secured on plate 60, and projects through an opening in chamber 54. Pin 58 and its associated plate 60 are electrically connected to plate 56, through compression spring 62.

Lead 52 is connected to one pole of any conventional electrosurgical generator. The other pole of the generator is connected to any suitable ground plate in contact with the patient's skin. The manner of establishing the electrical connection to provide for cauterizing tissue with the jaws 12 and 14 is well known to those skilled in the art and does not constitute a limitation on the present invention.

The tissue sampling device of this invention is used in the same manner as any conventional tissue sampling forceps of the prior art. When a sample of tissue is to be excised, the jaws 12 and 14 are opened to the position shown in FIG. 2. This is accomplished by sliding rod 22 rearwardly in the direction of arrow 64, to the position shown in FIG. 2. This opens jaws 12 and 14. The movement of the rod 22 to open the jaws can be accomplished by suitable handles at the rear end of the forceps. The exact mechanism for opening and closing the jaws is not a novel feature of this invention, and any suitable mechanisms known to the art can be used. Such mechanisms are shown in aforementioned U.S. Pat. Nos. 4,881,550 and 4,522,206, or in the other patents cited above.

When the rod 22 is slid rearwardly, it pivots the upper jaw 12 upwardly, around pins 28 and 32. The lower jaw 14 remains stationary.

Figure 2:
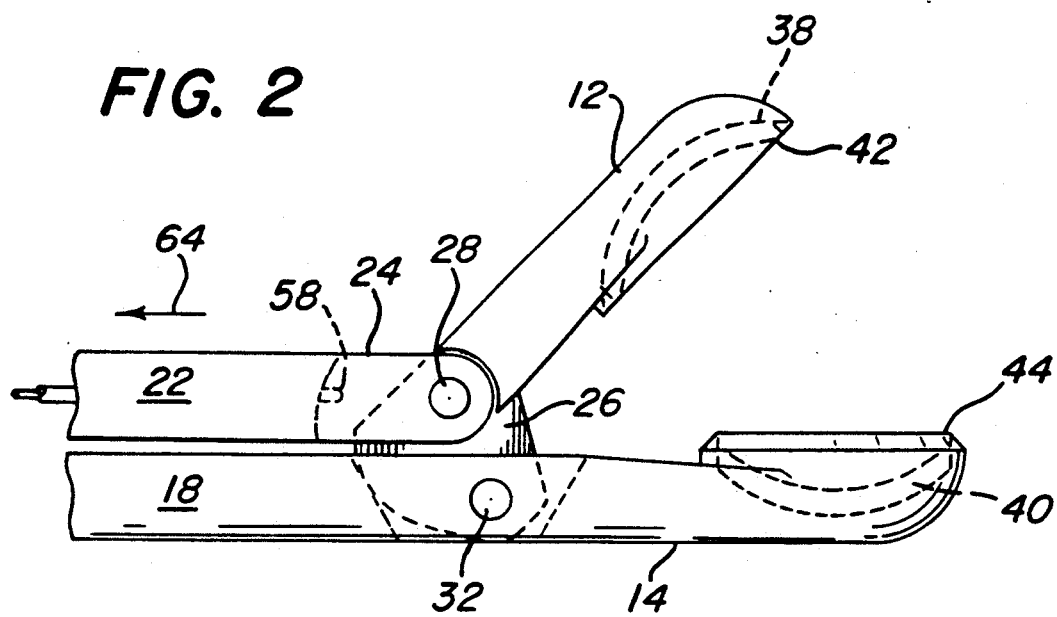
FIG. 2 is a side elevational view of the device shown in FIG. 1, but in the open position; and, FIG. 3 is an enlarged sectional view, taken along the line 3—3 of FIG. 1, and showing an enlargement of one section of the device.
Figure 3:
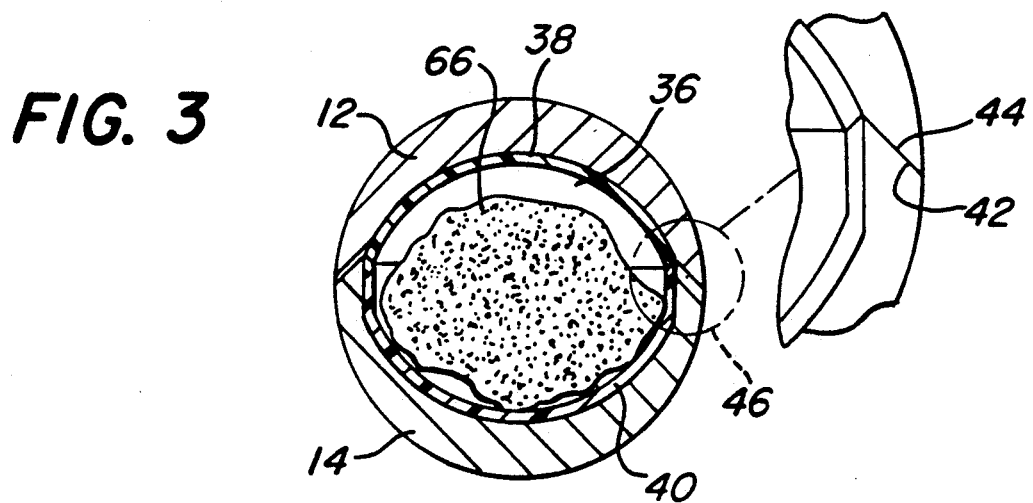

With the jaws in the position shown in FIG. 2, the tissue sought to be excised is located, and the handles on the forceps are moved in the direction opposite to the movement to open the jaws. This causes movable jaw 12 to move in the direction of stationary jaw 14. The beveled cutting edges 42 and 44 contact the tissue to be excised, and when the edges meet, a sample 66 of the tissue is excised, and is retained in the cavity 36. The complete closing of the jaws places the edges 42 and 44 of the jaws in a mating or abutting position, as shown in FIG. 3.

With the tissue sample 66 heat-insulated within the cavity 36, the electrosurgical generator is then activated, and this in turn heats the electrically contacting, upper and lower jaws 12 and 14. The rods 18 and 22, and jaws 12 and 14, are formed from stainless steel, or other electrically conductive metals. Sufficient heat is generated to cauterize the tissue at the area where the tissue sample was removed. The insulating liners or coatings 38 and 40 prevent any damage to the removed tissue sample. Thus, the jaws are heated only for a brief period, in order to provide the cauterization function. However, the insulating liners prevent any significant heat transfer to the tissue sample, thereby enabling the sample to remain unharmed during the cauterizing process.

It should also be noted that the insulating sleeves 30 and 34 prevent any heating of the rods 18 and 22 during cauterization. Electric current is passed to jaw 12 through contact with the rear edge of tab 26. The spring 62 ensures continuous electrical contact with the jaw 12.

The device 10 of this invention, as described above, is ideally suited for use as a laparoscopic biopsy device for taking tissue samples from a number of organs, e.g., liver, kidney, pancreas, etc. These devices generally have a shaft length of approximately 31 cm, and a diameter of approximately 5 mm.

The unique jaw arrangement of this invention can be employed in other types of tissue sampling and removal devices, such as in resectoscopes for various applications. For example, a resecting device having a hollow shaft approximately 12 mm in diameter and 31 mm long can be connected to a source of suction, in a conventional manner, for use in laparoscopically resecting a variety of organs. A shorter version of this latter device, on the order of 7 or 8 inches in length, can be employed for resecting rectal tumors, as well as for performing tonsillectomies and resecting other oral lesions. In all of these resection devices the hollow interior of the shaft is connected to a source of vacuum to permit the suction removal of the resected tissue.

It is thus seen that the devices of this invention accomplishes the multiple functions of excising a tissue sample, cauterizing the area where the sample was removed and protecting the excised tissue sample from the adverse effects of the cauterizing current.

Without further elaboration, the foregoing will so fully illustrate this invention that others may, by applying current or future knowledge, readily adapt the same for use under various conditions of service.

I claim:

1. A tissue sampling device comprising:
   (a) Means for removing tissue from an area of a living being comprising a pair of cutting jaws located at the first end of the device, the pair of cutting jaws being pivotally connected to permit the jaws to open and close, each of said cutting jaws comprising a peripheral cutting edge and a cavity to hold said tissue, said means further comprising actuating means for pivoting the cutting jaws between opened and closed positions;

(b) control means for cauterizing the direct area from which the tissue has been removed, after said tissue has been removed; and (c) means to prevent the cauterization of said tissue comprising heat insulating material forming the interior surface of said cavity.

2. The device of claim 1 wherein the heat insulating material is selected from the group comprising ceramic, plastic and rubber.

3. The device of claim 1 wherein the control means comprises a means to provide electrical energy to the jaws for heating the outer surfaces of the jaws when said jaws are closed to thereby cauterize tissue surrounding said jaws.

4. A method for removing a tissue sample from an area of a living being comprising the steps of:

(a) Providing an instrument with cutting jaws which forms a cavity for holding said tissue sample;

(b) providing an inner surface of heat insulating material to said cavity to insulate said tissue sample from the heat of cauterization;

(c) locating said instrument at a desired position for removing said tissue sample;

(d) operating said jaws to excise said tissue sample;

(e) applying heat, after said tissue sample is excised, to cauterize the wound caused by the excising of said tissue; and (f) removing said insulated tissue from said cavity for testing.

* * * * *